United States Patent
Glover et al.

(10) Patent No.: US 7,396,966 B2
(45) Date of Patent: Jul. 8, 2008

(54) OLEFINIC FEEDSTOCK TREATMENT PROCESSES

(75) Inventors: Bryan K. Glover, Algonquin, IL (US); Andrea G. Bozzano, Des Plaines, IL (US); Antoine Negiz, Wilmette, IL (US)

(73) Assignee: UOP LLC, Des Plaines, IL (US)

( * ) Notice: Subject to any disclaimer, the term of this patent is extended or adjusted under 35 U.S.C. 154(b) by 316 days.

(21) Appl. No.: 11/313,071

(22) Filed: Dec. 20, 2005

(65) Prior Publication Data

US 2007/0203387 A1      Aug. 30, 2007

(51) Int. Cl.
*C07C 2/64* (2006.01)
*C07C 5/327* (2006.01)
*C07C 7/12* (2006.01)
*C07C 4/08* (2006.01)

(52) U.S. Cl. .......... 585/323; 585/448; 585/826; 585/655; 585/483

(58) Field of Classification Search .......... 585/323, 585/826, 655, 448, 483
See application file for complete search history.

(56) References Cited

U.S. PATENT DOCUMENTS

| | | | |
|---|---|---|---|
| 5,276,231 A | 1/1994 | Kocal et al. | 585/323 |
| 5,300,715 A * | 4/1994 | Vora | 585/254 |
| 5,334,793 A | 8/1994 | Kocal | 585/323 |
| 6,740,789 B1 | 5/2004 | Bozzano et al. | 585/323 |
| 6,762,334 B1 | 7/2004 | Stewart et al. | 585/323 |

OTHER PUBLICATIONS

Pujado, Peter R., Linear Alkylbenzene (LAB) Manufacture *Handbook of Petroleum Refining Processes* 2nd Edition (1997) pp. 1.53-1.66.

Liggin, W.L., UOP Thermal Hydrodealkylation (THDA) Process *Handbook of Petroleum Refining Processes* 2nd Edition (1997) pp. 2.23-2.26.

* cited by examiner

*Primary Examiner*—Thuan Dinh Dang
(74) *Attorney, Agent, or Firm*—Arthur E Gooding

(57) ABSTRACT

Aromatic by-products are sorbed from mono-olefin-containing feedstocks of olefins having from about 6 to 22 carbon atoms per molecule that contain aromatic by-products having from 7 to 22 carbon atoms per molecule. A benzene-containing regenerant displaces and desorbs the aromatic by-products from the sorbent and a regeneration effluent is provided. The regeneration effluent is treated in a regeneration effluent distillation system to provide a benzene-rich stream and an aromatic by-products-containing stream. The latter is subjected to benzene-forming conditions and recycled to the regeneration effluent distillation system where benzene is recovered.

9 Claims, 4 Drawing Sheets

OLEFINIC FEEDSTOCK TREATMENT PROCESSES

FIELD OF THE INVENTION

This invention is an improvement in a process for the treatment of olefinic feedstocks, especially for making alkylated benzene compounds.

BACKGROUND OF THE INVENTION

Alkylbenzenes (phenyl-alkanes) are prepared by the alkylation of benzenes. Alkylbenzenes have found many utilities, the most prominent of which is to make alkylbenzene sulfonates for use in laundry detergents and similar products. The performance of the alkylbenzene sulfonate in a detergent composition will be affected by the nature of the alkyl group, for instance, its length and configuration, especially branching.

At one time, many household laundry detergents were made of branched alkylbenzene sulfonates (BABS). The standard process used by the petrochemical industry for producing branched alkylbenzene consists of oligomerizing light olefins, particularly propylene, to branched olefins having 10 to 14 carbon atoms per molecule and then alkylating benzene with the branched olefins in the presence of a catalyst such as HF. However, BABS were slow to biodegrade, and linear alkylbenzene sulfonates (LABS) and certain modified alkylbenzene sulfonates, which are referred to herein as MABS, which biodegrade more rapidly than BABS, are now used in many detergent formulations.

LABS are manufactured from linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid, acidic catalyst.

It is well known that aromatic by-products are formed during the catalytic dehydrogenation of paraffins. For instance, the article starting at page 86 of the Jan. 26, 1970 issue of "Chemical Engineering" states that the product of the dehydrogenation of linear paraffins includes aromatic compounds. Without limiting this invention in any way, these aromatic by-products are believed to include, for example, alkylated benzene, dialkylated benzene, naphthalenes, other polynuclear aromatics, diphenyl compounds, alkylated polynuclear hydrocarbons in the $C_{10}$-$C_{15}$ range, indanes, and tetralins. Typically, from about 0.2 to about 0.7 mass-percent, and generally to the extent of no more than 1 mass-percent, of the feed paraffinic compounds to a dehydrogenation zone form aromatic by-products. Although some commercially available dehydrogenation catalysts are more selective than others at minimizing the formation of aromatic by-products, it is believed that these by-products are formed at least to a small extent at suitable dehydrogenation conditions in the presence of most if not all commercially available dehydrogenation catalysts.

These aromatic by-products are believed to be deleterious in benzene alkylation processes, especially those using solid, acidic catalysts. First, some of the aromatic by-products may deposit on the surface of the catalyst and as mentioned above deactivate the catalyst. Second, some of the aromatic by-products are alkylated by mono-olefins to form heavy alkylate. Third, some of the aromatic by-products pass through the selective alkylation zone unreacted, are recovered with the overhead liquid stream of the paraffin column and are recycled to the dehydrogenation zone. These by-products can thus accumulate to unacceptable concentrations. In the prior art processes employing a solid alkylation catalyst, the concentration of aromatic by-products in the stripping effluent stream can typically accumulate to 4 to 10 mass-percent, which leads to rapid deactivation of solid alkylation catalyst. Where the alkylation catalyst is HF in the prior art processes, the concentration of aromatic by-products in the stripping effluent stream can typically accumulate to 3 to 6 mass-percent.

Processes for removing the aromatic by-products that are formed during the catalytic dehydrogenation of paraffins are also known. Aromatic by-products, however, are difficult to separate using conventional distillation techniques due to the similarity in boiling points the paraffins and olefins. Suitable aromatics removal zones may be selected from any processing methods that exhibit the primary requirement of selectivity for the aromatic by-products. Suitable aromatics removal zones include, for example, sorptive separation zones and liquid-liquid extraction zones. See U.S. Pat. Nos. 5,276,231 and 5,334,793, the contents of each are incorporated herein by reference. Where the aromatics removal zone is a sorptive separation zone, a fixed bed or a moving bed sorbent system may be used, but the fixed bed system is more common. The sorbent usually comprises a particulate material.

In a fixed bed system, the sorbent is typically installed in one or more vessels in a parallel flow arrangement, so that when the sorbent bed in one vessel is spent by the accumulation of the aromatic by-products thereon, the spent vessel is bypassed while continuing uninterrupted operation through another vessel. A purge stream comprising a purge component, such as $C_5$ or $C_6$ paraffin (e.g., normal pentane), is passed through the spent sorbent bed in the bypassed vessel in order to purge or displace or sweep unsorbed components of the stream containing the aromatic by-products from the void volume between particles of sorbent. The purge component is sometimes referred to herein as the sweep fluid. After purging, a regenerant or desorbent stream comprising a desorbent component such as benzene is passed through the sorbent bed in the bypassed vessel in order to desorb aromatic by-products from the sorbent. Following regeneration, the sorbent bed in the bypassed vessel is again available for use in sorbing aromatic by-products.

Thus, a sorptive separation zone for removing the aromatic by-products typically produces three effluents, which approximately correspond to each of the three steps in the cycle of sorption, purge, and desorption. The composition of each of the three effluents changes during the course of each step. The first effluent, the sorption effluent, contains unsorbed components (i.e., paraffins and olefins) of the stream from which the aromatic by-products are removed, and also typically contains the desorbent component. With its decreased amount of aromatic by-products relative to the stream that is passed to the sorptive separation zone, this effluent is used further along in the process to produce alkylbenzenes. For example, if the stream that passes to the sorptive separation zone is the dehydrogenation zone effluent, the sorption effluent contains mono-olefins and paraffins and thus passes directly to the alkylation zone.

The second effluent, the purging effluent, contains the purge component, unsorbed components of the stream from which the aromatic by-products were sorbed, and often the desorbent component. The purging effluent is sometimes referred to herein as the sweep effluent. The third effluent is the desorption effluent, which contains the desorbent component, the aromatic by-products, and the purge component. In the typical prior art process, the purging and desorption effluents are separated in two distillation columns. The desorption effluent passes to one column, which produces an overhead stream containing the desorbent and purge components and a bottom stream containing the aromatic by-products which is rejected from the process. The overhead stream of the first column and the purging effluent pass to a second column, which separates the entering hydrocarbons into an overhead stream containing the purge component and a bottom stream containing the desorbent component and unsorbed components of the stream from which the aromatic by-products are removed. The overhead stream of the second column is used as the purge stream. The bottom stream of the second column is used in the process to produce alkylbenzenes. In the example described above where the stream that passes to the sorptive separation zone is the dehydrogenation zone effluent, the bottom stream of the second column contains benzene, mono-olefins, and paraffins and flows directly to the alkylation zone. U.S. Pat. No. 6,762,334 discloses the use of a divided wall column to effect in one column the two distillations described above.

The aromatic by-products are usually burned for fuel value or exported as a low value feedstock to an aromatics unit for recovering benzene, toluene and xylene values. Hence, the stream has little value. Thus, not only do the aromatic by-products represent a loss of paraffin feedstock, but also, costs must be incurred to remove these aromatic by-products from the olefin-containing stream. Accordingly, dehydrogenation conditions have been used to minimize the production of the aromatic by-products. Accordingly, the olefin-containing feedstock to an alkylation reactor often contains about 90 mass-percent paraffins. Unfortunately, this has resulted in inefficiencies in the process for making alkylbenzenes. While paraffins are relatively inert to the alkylation reaction, they must be removed from the alkylbenzene reaction product to meet product specifications. Typically the paraffins are removed from the alkylbenzenes by distillation under substantial vacuum, e.g., from about 2 kpa(absolute) (hereinafter kPa(a)) (0.3 psi(absolute) (hereinafter psi(a))) to 10 kpa(a) (1.5 psi(a)) to avoid distillation temperatures that can degrade alkylbenzenes. And the sizable concentration of paraffins in the alkylation reaction product renders their removal by distillation a significant capital and operating cost in the overall process.

SUMMARY OF THE INVENTION

In accordance with this invention processes are provided to treat an olefin-containing feedstock that contains aromatic by-products to economically generate benzene. Advantageously the generated benzene is provided in a form suitable for use as a feed, e.g., to an alkylation reactor. In preferred aspects of the processes of the invention, the olefin-containing feedstock is derived from the dehydrogenation of paraffins, and advantageously, the dehydrogenation is conducted under conditions to enhance the olefin-to-paraffin ratio, e.g., provide less than about 85 mass-percent paraffins, in the dehydrogenation effluent. Although the more severe dehydrogenation conditions will lead to the increased production of aromatic by-products, the ability to generate benzene from the aromatic by-products provides an overall economically attractive process, especially for the production of alkylbenzene.

The broad aspects of this invention pertain to continuous processes for removing aromatic by-products from a feedstock containing aliphatic mono-olefin having from 6 to 22 carbon atoms per molecule and aromatic by-products having from 7 to 22 carbon atoms per molecule by:

a) selectively removing at least a portion of the aromatic by-products from the feedstock by at least intermittently passing at least a portion of the feedstock to an on-stream zone containing sorbent at conditions effective to selectively sorb aromatic by-products on the sorbent and to produce a sorption effluent stream comprising the mono-olefins and having a reduced concentration of aromatic by-products;

b) regenerating sorbent in an off-stream zone containing sorbent, the sorbent in the off-stream zone having aromatic by-products sorbed thereon from having been on-stream in step a, said regeneration comprising at least intermittently passing a regenerant comprising benzene to the off-stream zone to desorb aromatic by-products from the sorbent and produce a regeneration effluent comprising benzene and aromatic by-products;

c) distilling in a regeneration effluent distillation system at least a portion of the regeneration effluent to provide at least one overhead containing benzene and at least one higher-boiling fraction containing desorbed aromatic by-products;

d) subjecting at least intermittently at least a portion of the at least one higher-boiling fraction to benzene-forming conditions to convert aromatic by-products to benzene and provide a conversion effluent containing benzene; and e) distilling in the regeneration effluent distillation system at least a portion of the conversion effluent.

Another aspect of this invention is an integrated paraffin dehydrogenation and benzene alkylation process. This aspect of the invention comprises:

a) dehydrogenating a feedstock comprising a paraffin having from 6 to 22 carbon atoms per molecule in a dehydrogenation zone and recovering therefrom a dehydrogenated product comprising a mono-olefin, less than 85, preferably less than about 70, mass-percent paraffins, benzene and at least about 2, preferably at least about 3, mass-percent aromatic by-products having from 7 to 22 carbon atoms per molecule;

b) selectively removing at least a portion of the aromatic by-products from at least a portion of the dehydrogenated product by at least intermittently passing at least a portion of the dehydrogenated product to an on-stream zone containing sorbent at conditions effective to selectively sorb aromatic by-products on the sorbent and to produce a sorption effluent stream comprising the mono-olefin and the paraffin and having a reduced concentration of aromatic by-products;

c) regenerating the sorbent in an off-stream zone containing sorbent, the sorbent in the off-stream zone having aromatic by-products sorbed thereon from having been on-stream in step b, said regeneration comprising at least intermittently passing a regenerant containing benzene to the off-stream zone to desorb aromatic by-products from the sorbent and produce a regeneration effluent comprising benzene and aromatic by-products;

d) distilling in a regeneration effluent distillation system at least a portion of the regeneration effluent to provide at least one overhead containing benzene and at least one higher-boiling fraction containing desorbed aromatic by-products;

e) subjecting at least intermittently at least a portion of the at least one higher-boiling fraction to benzene-forming conditions to convert aromatic by-products to benzene and provide a conversion effluent containing benzene;

f) distilling in the regeneration effluent distillation system at least a portion of the conversion effluent;

g) alkylating benzene with at least a portion of the sorption effluent stream under alkylation conditions including a stoichiometric excess of benzene to provide an alkylation effluent comprising the alkylbenzene, the paraffin and benzene; and h) passing at least intermittently at least a portion of the at least one overhead containing benzene from step d to step g.

In this aspect of the invention, the dehydrogenation is preferably conducted under conditions such that the sorption effluent of step a comprises mono-olefin and paraffin in a mole ratio of greater than 1:7, more preferably greater than about 1:6, say, 1:6 to 2:1. Advantageously, prior to step b the dehydrogenated product is subjected to selective hydrogenation conditions including the presence of selective hydrogenation catalyst and hydrogen, said conditions being capable of selectively hydrogenating diolefins to mono-olefins.

In yet another aspect of the invention, continuous processes are provided for removing aromatic by-products from a feedstock containing an aliphatic mono-olefin having from 6 to 22 carbon atoms per molecule, an aliphatic paraffin having from 6 to 22 carbon atoms per molecule and aromatic by-products having from 7 to 22 carbon atoms per molecule and alkylating benzene with the aliphatic mono-olefin having aromatic by-products removed therefrom by:

a) selectively removing at least a portion of the aromatic by-products from the feedstock by at least intermittently passing at least a portion of the feedstock to an on-stream zone containing sorbent at conditions effective to selectively sorb aromatic by-products on the sorbent and to produce a sorption effluent stream comprising the mono-olefin and the paraffin and having a reduced concentration of aromatic by-products;

b) regenerating sorbent in an off-stream zone containing sorbent, the sorbent in the off-stream zone having aromatic by-products sorbed thereon from having been on-stream in step a, said regeneration comprising at least intermittently passing a regenerant comprising benzene to the off-stream zone to desorb aromatic by-products from the sorbent and produce a regeneration effluent comprising benzene and aromatic by-products;

c) distilling in a regeneration effluent distillation system at least a portion of the regeneration effluent to provide a vapor phase overhead containing benzene and a liquid phase including a higher-boiling fraction containing desorbed aromatic by-products;

d) subjecting at least intermittently at least a portion of the higher-boiling fraction to benzene-forming conditions to convert aromatic by-products to benzene and provide a conversion effluent containing benzene;

e) distilling in the regeneration effluent distillation system at least a portion of the conversion effluent, wherein steps c, d and e comprise a flow cycle loop;

f) at least intermittently withdrawing purge from at least one point in the flow cycle loop in an amount sufficient to avoid undue buildup of aromatic by-products in the flow cycle loop;

g) reacting mono-olefin contained in the sorption effluent stream with a stoichiometric excess of benzene under alkylation conditions to provide an alkylation reaction effluent containing an alkylbenzene, the paraffin, benzene and heavies;

h) separating by distillation benzene from at least a portion of the alkylation reaction effluent to provide a benzene overhead and a first liquid stream containing the paraffin, the alkylbenzene and heavies;

i) separating by distillation the paraffin from at least a portion of the first liquid stream to provide a paraffin overhead and a second liquid stream containing the alkylbenzene and heavies; and j) separating by distillation the alkylbenzene from at least a portion of the second liquid stream to provide an alkylbenzene overhead and a third liquid stream containing heavies; and k) passing at least a portion of the heavies in the third liquid stream to the flow cycle loop of steps c, d and e.

Heavies are dimers, dialkylaryl compounds and diaryl compounds. These compounds can be formed under alkylation conditions. Preferably at least a portion of the benzene-containing overhead of step c is vapor phase and is passed to step g.

DETAILED DESCRIPTION

Figure 1:
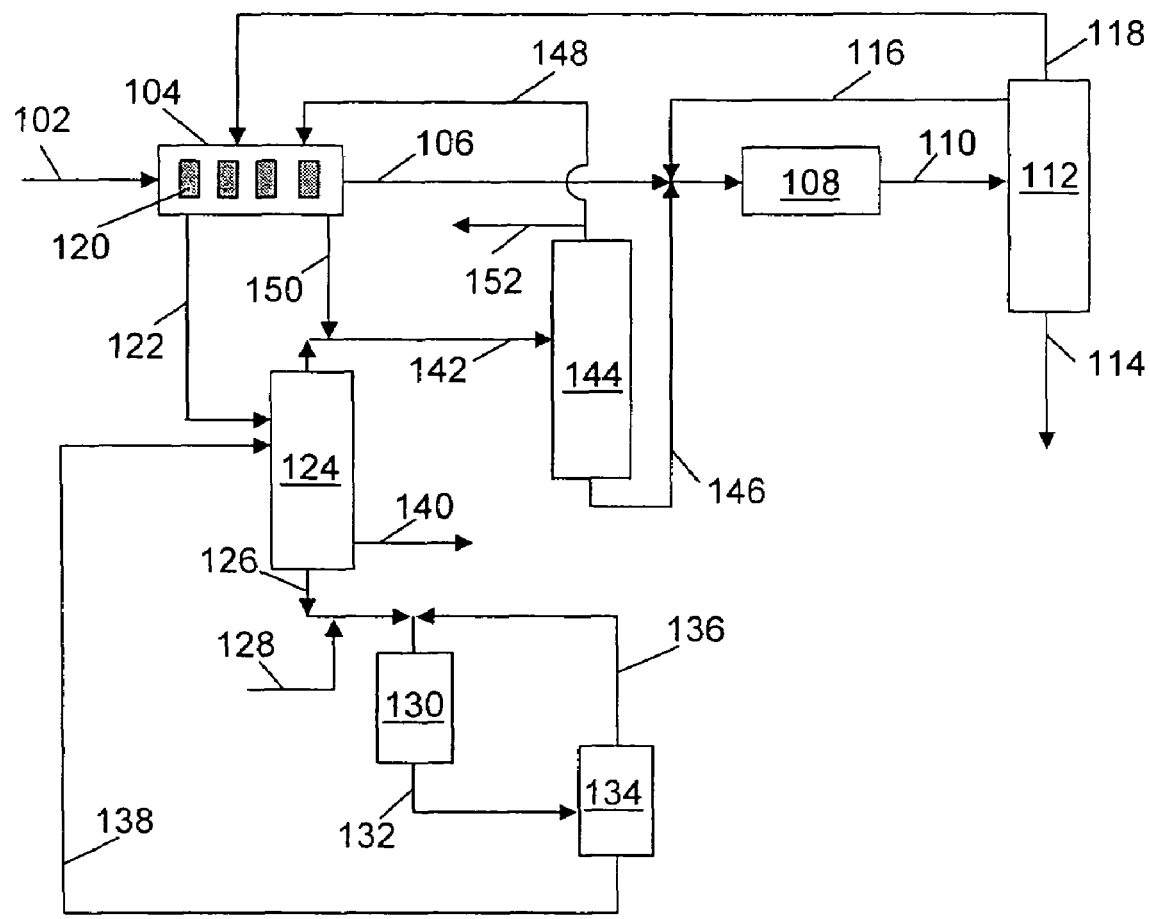
FIG. 1 is a schematic depiction of a process flow scheme in accordance with this invention for treating an olefin-containing feedstock.

In accordance with the processes of this invention, an aliphatic, mono-olefin-containing feedstock containing mono-olefin having from about 6 to about 22 carbon atoms per molecule and aromatics having from about 7 to about 22 carbon atoms per molecule is treated to provide a product containing mono-olefin and having a reduced concentration of aromatics and to provide benzene from such aromatics. The mono-olefin-containing feedstock may be derived from any convenient source and may contain components other than olefin and aromatics such as lighter mono-olefins, diolefins, paraffins, halogenated hydrocarbons, and oxygenated hydrocarbons such as aldehydes, ethers, esters and carboxylic acids.

The concentration of mono-olefin having from 6 to 22 carbon atoms per molecule can vary widely, but is most often at least about 1, say, about 1 to 98 mass-percent based upon the total mass of the feedstock. Where the feedstock is from the catalytic dehydrogenation of paraffin, the olefin is usually in an amount of about 5 to 30, and more frequently about 9 to 20, mass-percent of the feedstock. Such feedstocks will contain as the predominant component, unreacted paraffins, e.g., from about 50 to 90, mass-percent based upon the feedstock. Of course, other olefin synthesis procedures such as dehydration of alcohols and dechlorination, can provide the olefin-containing feedstock. Feedstocks from such sources may have little, if any, paraffin.

The aromatics contained in the feedstocks are referred to herein as aromatic by-products as such aromatics are normally contained in the effluent from a catalytic paraffin dehydrogenation; however, for the broad purposes of this invention it is not essential that the aromatics actually be by-products. The aromatic by-products can comprise substituted phenyl compounds such as toluene, xylenes, and higher methylated benzenes; ethylbenzene, diethylbenzene, and triethylbenzenes; isopropylbenzene (cumene), n-propylbenzene, and higher propylbenzenes; butylbenzenes; and pentylbenzenes and the like; biphenyl compounds and substituted biphenyl compounds; and fused ring compounds and substituted fused ring compounds such as napthalenes, indanes, tetralins, and the like. Where the feedstocks are used to make alkylbenzenes and a paraffin-containing stream is generated during the purification of the alkylbenzenes and is recycled to the dehydrogenation, the feedstocks may also contain alkylbenzenes. In many instances, the aromatic by-products have the same carbon number as the mono-olefins. The concentration of the aromatic by-products can vary widely, e.g., from about 0.5 to 30 or 50 mass-percent based upon the mass of the feedstock. Especially where the feedstock is from the catalytic dehydrogenation of paraffins, aromatic by-products are present in an amount of about 1 to 20, preferably 2 or 3 to 15, mass-percent of the feedstock.

The processes of this invention are particularly attractive for the treatment of mono-olefin-containing feedstocks for the production of alkylbenzenes. For these uses, the olefin-containing aliphatic compound is preferably of about 8 to 19, often for detergent applications, 9 to 16, carbon atoms per molecule. The positioning of the olefinic bond in the molecule is not critical as most alkylation catalysts have been found to promote migration of the olefinic bond. Linear olefins and those with some branching, such as the lightly branched modified alkylbenzenes such as described in U.S. Pat. No. 6,187,981, are usually desired for alkylbenzenes for detergent applications. The olefin-containing aliphatic compound is usually a mixture of two or more olefins.

The processes of this invention are particularly attractive where the source of the olefin feedstock is obtained by the catalytic dehydrogenation of paraffin. In dehydrogenation operations, a heated feed stream containing paraffins is passed through a bed of a suitable catalyst maintained at dehydrogenation conditions of hydrogen concentration, temperature, pressure, etc. The effluent of this catalyst bed or reactor effluent stream is usually cooled, partially condensed, and passed to a vapor-liquid or product separator. The condensed material, referred to herein as the dehydrogenated product stream, is passed to a stripping separation zone which usually includes a stripping column that removes all compounds which are more volatile than the lightest normal hydrocarbon which it is desired to charge to the alkylation section of the process. The stripping column produces a net bottoms stream referred to herein as the stripping effluent stream.

The source of the paraffinic feed for dehydrogenation is not critical although certain sources of paraffin will likely result in the impurities being present. Conventionally, kerosene fractions produced in petroleum refineries either by crude oil fractionation or by conversion processes therefore form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds. The paraffinic feedstock may alternatively be at least in part derived from oligomerization or alkylation reactions. Another source of paraffins is in condensate from gas wells. Usually insufficient quantities of such condensate are available to be the exclusive source of paraffinic feedstock. However, its use to supplement other paraffinic feedstocks can be desirable. Paraffins may also be produced from synthesis gas (Syngas), hydrogen and carbon monoxide. This process is generally referred to as the Fischer-Tropsch process.

Paraffin dehydrogenation processes are described in Peter R. Pujado, UOP Pacol Dehydrogenation Process, in Handbook of Petroleum Refining Processes, Second Edition, Editor Robert A. Meyers, McGraw-Hill, New York, USA (1997), at pp. 5.11 to 5.19, the teachings of which are incorporated herein by reference. Dehydrogenation conditions are selected to minimize cracking and polyolefin by-products. Catalytic dehydrogenation is subject to equilibrium reactions. To achieve dehydrogenation products having higher concentrations of olefins, higher temperatures are required. However, at these higher temperatures, thermal cracking is increased and the formation of aromatic by-products is greater. Accordingly, milder dehydrogenation conditions have been often used to minimize the loss of paraffin to cracking products and to aromatic by-products. Especially where the olefin-containing feedstock is ultimately to be used for making LABS or MABS, dehydrogenation conditions are preferred that will not result in any appreciable isomerization of the hydrocarbons.

The processes of this invention, by recovering benzene from the aromatic by-products, enable more severe catalytic dehydrogenation conditions to be used while still obtaining an economically viable process for making alkylbenzenes. Although a greater portion of the paraffin feed to the catalytic dehydrogenation is converted to aromatic by-products, benzene, a raw material used in the alkylation, is obtained and the loss of aromatic by-products to, say, fuel, is reduced. Additionally, the molar ratio of mono-olefin to paraffin in the dehydrogenation product is increased. As the separation of paraffins from olefins of the same carbon numbers is difficult, a substantial amount of paraffins pass though the alkylation reaction and alkylbenzene refining system, requiring appropriate equipment size and energy consumption in heat exchange and distillation unit operations.

In preferred processes of this invention, the dehydrogenation is conducted to yield about 12 to 25, more preferably 14 to 20, mass-percent mono-olefins in the dehydrogenation product. The paraffin is present in the dehydrogenation product in an amount of less than about 80, more preferably less than about 70, mass-percent.

The catalysts used for dehydrogenation are not critical to the processes of this invention. Many types of dehydrogenation catalysts are known as exemplified by U.S. Pat. Nos. 3,274,287; 3,315,007; 3,315,008; 3,745,112; and 4,430,517. Often the dehydrogenation catalysts are platinum group metal containing catalysts. One preferred catalyst is a layered composition comprising an inner core and an outer layer bonded to the inner core, where the outer layer comprises a refractory inorganic oxide having uniformly dispersed thereon at least one platinum group (Groups 8-10 of the periodic table) metal and at least one promoter metal, and where at least one modifier metal is dispersed on the catalyst composition.

The dehydrogenation may be conducted in the liquid phase or in a mixed vapor-liquid phase, but preferably in the vapor phase. Typical dehydrogenation conditions involve a temperature of from about 400° C. (752° F.) to about 900° C. (1652° F.) and preferably from about 420° C. (788° F.) to about 550° C. (1022° F.). Generally for normal paraffins, the lower the molecular mass the higher the temperature required for comparable conversion. Pressures are generally from about 1 kpa(g) (0.15 psi(g)) to about 1000 kpa(g) (145 psi(g)), preferably between about 100 kpa(g) (14.5 psi(g)) and 400 kpa(g) (58.0 psi(g)), and a LHSV of from about 0.1 to about 100 hr$^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units.

If desired, the dehydrogenation product may be subjected to selective hydrogenation to convert diolefins to mono-olefins. U.S. Pat. No. 5,276,231, for instance, discloses the selective hydrogenation of diolefinic by-products from dehydrogenation.

In the processes of this invention at least a portion of the aromatic by-products in the mono-olefin-containing feedstock is removed using at least one aromatics removal zone. An aromatics removal zone may be placed in one or more locations. For instance, where the feedstock is obtained from a catalytic dehydrogenation including a selective diolefin hydrogenation zone, the aromatic by-products may be selectively removed before or after the selective hydrogenation.

Suitable aromatics removal zones for this embodiment of the invention include sorptive separation zones. Sorptive separation zones include fixed bed or moving or fluidized sorbent bed systems, but the fixed bed system is preferred. The sorbent may be installed in one or more vessels and in either series or parallel flow. The flow of the feedstock containing the aromatic by-products through the sorptive separation zones is preferably performed in a parallel manner so that one or more sorption beds can be undergoing regeneration while one or more beds are removing aromatic by-products.

Suitable sorbents may be selected from materials which exhibit the primary requirement of selectivity for the aromatic by-products and which are otherwise convenient to use. Suitable sorbents include, for example, molecular sieves, silica, activated carbon activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. The preferred sorbent is a molecular sieve, and the preferred molecular sieve is 13 X zeolite (sodium zeolite X).

Those skilled in the art are able to select the appropriate conditions for operation of the sorbent without undue experimentation. For example, a fixed bed sorptive separation zone containing 13 X zeolite may be maintained at a temperature generally from about 20° C. (68° F.) to 300° C. (572° F.), and preferably from about 100° C. (212° F.) to 200° C. (392° F.), a pressure effective to maintain the stream containing the aromatic by-products in a liquid phase at the chosen temperature, and a liquid hourly space velocity from about 1 hr$^{-1}$ to about 10 hr$^{-1}$ and preferably from about 1 hr$^{-1}$ to about 3 hr$^{-1}$. The flow of the feedstock through a fixed or moving sorption bed may be conducted in an upflow, downflow or radial-flow manner.

Although both liquid and vapor phase operations can be used in many sorptive separation processes, liquid phase operation is preferred for the sorptive separation zone because of the lower temperature requirements and because of the higher sorption yields of the aromatic by-products that can be obtained with liquid phase operation over those obtained with vapor phase operation. Therefore, the temperature and pressure of the sorptive separation are preferably selected to maintain the feedstock in a liquid phase. The resulting unsorbed stream having a reduced concentration of aromatic by-products is a desorption effluent. However, the operating conditions of a sorptive separation zone can be optimized by those skilled in the art to operate over wide ranges which are expected to include the conditions in the reaction zones of the invention and its variants. Therefore, a sorptive separation zone may be contained in a common reaction vessel with the dehydrogenation zone, the selective diolefin hydrogenation zone, or the selective alkylation zone.

A sorbent bed is periodically subjected to regeneration conditions. A benzene-containing stream is use for the regeneration. Generally it is preferred that the benzene be highly pure to avoid undue sorption of any impurities on the sorbent during regeneration. Nevertheless, the regenerant may contain components that do not materially interfere with the regeneration and are acceptable in the sorption effluent. For integrated processes where the sorption effluent is used as a feed to a benzene alkylation reactor and benzene from the refining system is used as regenerant, to prevent undue buildup of paraffins in the regeneration effluent distillation system, the regenerant should contain less than 0.1 mass-percent paraffins, more preferably less than 100 mppm (mass part per million) paraffins, and even more preferably less than 10 mppm paraffins. Typically the regenerant contains at least about 50, preferably at least about 90 or 99, more preferably to at least 99.5, to essentially 100, mass-percent benzene. A purge may be intermittently or continuously withdrawn from at least one point in the recycle loop consisting of the sorber assembly and the regeneration effluent distillation system in order to avoid excessive concentrations of paraffins. Where the sorption effluent is used as a feed to an alkylation reactor to make alkylbenzene, the regenerant is conveniently a pure benzene stream from the refining of the alkylbenzene-containing reaction effluent. Any suitable regeneration method may be used, including altering the temperature and pressure of the sorbent and treating with liquid or vaporous or mixed phase regenerant to displace or desorb aromatic by-products.

A regeneration effluent is withdrawn from the aromatics removal zone which contains benzene, a purge hydrocarbon such as pentanes if the zone was purged with a purge hydrocarbon prior to being contacted with the benzene column overhead stream, and aromatic by-products. This regeneration effluent stream is passed to a regeneration effluent distillation system. The regeneration effluent distillation system may be a single column or may be two or more column in parallel or in series. The regeneration effluent distillation system produces a net overhead stream that contains benzene. If a purge compound is used such as pentane in the regeneration of sorbent, the distillation assembly is typically provided with distillation capability to separate the purge compound from benzene, as well as capacity to separate the purge compound from paraffins and mono-olefins of the mono-olefin feedstock that have been purged from the sorbent. These separations may be done in the same or a different column than the separation of benzene from aromatic by-products.

Accordingly, in an integrated process for the production of alkyl aromatics that uses dehydrogenation and an aromatics removal zone, and an alkylation section which employs a benzene rectifier and a benzene column for recovering the alkyl aromatics, a preferred embodiment of this invention is one in which the regeneration method for the sorbent in the aromatics removal zone comprises altering the temperature and pressure of the sorbent and treating the sorbent with a liquid to displace or desorb the sorbed aromatic by-products.

The regeneration effluent distillation stream provides a bottoms fraction containing aromatic by-products that had be desorbed from the sorbent during regeneration. A bottoms fraction as contemplated herein, may be the liquid at the bottom of a distillation column or may be a side-draw from a lower portion of the column.

In accordance with the processes of this invention, at least a portion of this bottoms fraction is subjected to benzene-forming conditions to provide benzene. Suitable dealkylation processes for benzene-forming include hydrodealkylation, steam dealkylation, oxidative dealkylation in combination with steam or among others. Hydrodealkylation can be thermal and or catalytic. Thermal hydrodealkylation is preferred. The benzene-forming conditions are preferably sufficient to dealkylate at least about 70, more preferably at least about 85, and sometimes between about 85 and 98, mass-percent of the aromatic by-products.

In general, hydrodealkylation conditions include elevated temperatures and pressures, e.g., about 200° C. (392° F.) to 700° C. (1292° F.) and 100 kpa(g) (14.5 psi(g)) to 5000 kPa(g) (725 psi(g)) and the presence of hydrogen, e.g., from about 1:1 to 50:1 moles of hydrogen per mole of aromatic by-products. Thermal hydrodealkylation is typically at temperatures of between about 500° C. (932° F.) or 575° C. (1067° F.) and 700° C. (1292° F.). Often the pressures of thermal hydrodealkylation are in the range of about 2500 kPa(g) (363 psi(g)) to 3500 kPa(g) (508 psi(g)). Exemplary thermal hydrodealkylation conditions are described in, for instance, W. L. Liggin, UOP Thermal Hydrodealkylation (THDA) Process, in Handbook of Petroleum Refining Processes, Second Edition (1997), at pp. 2.23 to 2.26.

Catalytic hydrodealkylation conditions are generally milder than those used for thermal hydrodealkylation. Temperatures of about 200° C. (392° F.) to 600° C. (1112° F.), say, 250° C. (482° F.) to 550° C. (1022° F.), are often employed. Pressures are generally in the range of about 100 kpa(g) (14.5 psi(g)) to 3500 kpa(g) (508 psi(g)). Often, the milder catalytic hydrodealkylation conditions will result in less cracking of the alkyl groups removed from the aromatic by-products, that is, light ends may contain a lesser concentration of methane than would occur from a thermal hydrodealkylation. Hence, less hydrogen may be required, e.g., from about 1 to 10 moles of hydrogen per mole of aromatic by-products. Any suitable hydrodealkylation catalyst may be used. Typical catalysts are acidic catalysts including aluminas, silicas, silica aluminas such as zeolites including dealuminated Y, silicalite, zeolites having the MOR framework type, zeolite beta, ZSM-5, zeolite having the MTW framework type, UZM-4, UZM-5, UZM-8, UZM-16; silica aluminophosphates such as SAPO-34, SAPO-11, SAPO-31, SAPO-5, SAPO-18, MAPSO-43; which may be supported or unsupported. References herein to zeolite framework types are to those in the *Atlas of Zeolite Framework Types*, Fifth Revised Edition, 2001, Elsevier, New York, USA. UZM-4 is described in U.S. Pat. No. 6,419,895, herein incorporated by reference in its entirety. UZM-5 and UZM-6 are described in U.S. Pat. Nos. 6,613,302 and 6,388,157, which are herein incorporated in their entireties by reference. UZM-8 is described in U.S. Pat. No. 6,756,030, herein incorporated by reference in its entirety. UZM-16 is described in U.S. Pat. No. 6,752,980, herein incorporated by reference in its entirety. In some instances, the catalyst is halogenated, e.g., fluorided or chlorided, to enhance acidity. The catalyst may also comprise one or more adjuvants or agents which may serve as catalysts, promoters and activity modifiers. Active metals can be from Groups 4, 5, 6, 7, and 8 to 10 of the periodic table, such as platinum and rhenium.

Promoters and/or activity modifiers can be selected from Groups 1, 2, 13, 14, 15, and 16 of the periodic table, such as tin, lead, germanium, and sulfur. References herein to the periodic table are to the new IUPAC notation as shown on the Periodic Table of the Elements in the inside front cover of the CRC Handbook of Chemistry and Physics, 80th Edition, 1999-2000, CRC Press, Boca Raton, Fla., USA.

As the benzene-forming conditions typically involve the presence of hydrogen, preferred processes of this invention recover unreacted hydrogen from the product of the benzene-forming conditions for recycle. Generally this recovery is done by gas/liquid phase separation.

A benzene product stream is generated as a result of subjecting the bottoms fraction to benzene-forming conditions. This stream will contain benzene and conversion products of the dealkylation. Lights such as methane, ethane, propane, and the like that have been removed from the phenyl ring can be removed from the benzene in the benzene product stream by distillation, including flash distillation, or by liquid gas separation where the conditions of the product stream are not adequate to maintain the lights in the liquid stream. If desired, at least a portion of the lights can be maintained with the benzene product stream for recycling to the regeneration effluent distillation system.

At least a portion of the benzene product stream is recycled to the regeneration effluent distillation system, which system provides an overhead stream containing benzene. Thus the benzene generated by the benzene-forming conditions will be recovered. Similarly, unreacted aromatic by-products will be returned to the bottoms fraction and are recycled to the dealkylation.

The net overhead stream containing benzene recovered from the regeneration effluent distillation system can have a number of uses. Contaminants in the stream can include lights and aromatic by-products, and each of the uses is not equivalent in terms of the levels of components other than benzene that are acceptable in the net overhead stream. For example, when passed to the alkylation reactor for alkylation the purity of the net overhead stream could be relatively low. The purity could be relatively high when the stream is used to regenerate catalyst in the alkylation reactor, and the purity could be moderate when the stream is used as regenerant in the sorptive separation zone. In an embodiment in which a very pure net overhead stream is required, aromatic by-products may be substantially absent from the stream. As used herein a component is substantially absent from a stream when the stream contains less than 1 mass-% of the component.

In some embodiments of the processes of the invention, in order to provide a stable operation, i.e., avoid an undue buildup or excessive accumulation in the recycle loop, a purge is intermittently or continuously withdrawn from at least one point in the recycle loop. Most often, a purge is withdrawn from the regeneration effluent distillation system. This purge may be taken from at least one of above or below the point where the bottoms fraction is withdrawn. For instance, if the benzene-forming conditions result in a low conversion of toluene to benzene but a higher conversion of higher alkyl substituted benzenes, then a purge of the lighter toluene may be taken above the point that the higher boiling bottoms fraction is withdrawn from the distillation system. Similarly, if higher boiling aromatic by-products tend to buildup in the recycle loop, a purge from a lower point in the regeneration effluent distillation system may be taken.

Withdrawing a purge from the recycle loop defined by the regeneration distillation system and the dealkylation reactor is an option that can prevent undue buildup in the recycle loop of certain components that might have a deleterious effect in the dealkylation reactor. Typically, the amount that would be purged is not constrained by the dealkylation reaction but can reduce the amount of coke formation in the dealkylation reactor. For instance, if the benzene-forming conditions result in a low conversion of a component, then recycling that component to the dealkylation reactor might eventually lead to coke deposits in the dealkylation reactor or on the dealkylation catalyst if present. Purging such a component could be advisable. On the other hand, recycling certain other components to the dealkylation reactor may be beneficial. For instance in a benzene-forming hydrodealkylation reactor, bi-cyclic aromatics such as diphenylalkanes are generally considered undesirable by-products that reduce benzene yield. However, recycling bi-cyclic aromatics can inhibit their further formation. As for aromatic by-products, it might be advisable to purge them if they lead to excessive coke deposition. On the other hand it might be advisable to recycle them if they do not cause coke deposition or if purging them would coincidentally purge too many co-boiling bi-cyclic aromatics.

The generated and recovered benzene may be used for any purpose. As benzene is a raw material for the production of alkylbenzenes, the process of this invention is particularly beneficial when integrated with a benzene alkylation unit. The lights and purge can similarly be used for any suitable purpose. However, most often, they would be used for fuel value due to the low volume of the streams after benzene was generated and recovered.

When the processes of this invention employ a hydrodealkylation step followed by distillation to remove lights, an additional benefit exists. Impure benzene feedstreams, that is, those streams that may contain one or more of higher aromatics, aliphatics (including paraffins and olefins), sulfur compounds, nitrogen compounds, and the like, can also be treated by the hydrodealkylation. The impure benzene feedstream can be introduced at any convenient point in the cycle loop.

In preferred aspects of this invention, the mono-olefin-containing feedstock is used for making alkylbenzenes. Various processes have been proposed for the alkylation of benzene. See, for instance, Peter R. Pujado, Linear Alkylbenzene (LAB) Manufacture, in Handbook of Petroleum Refining Processes, Second Edition (1997), at pp. 1.53 to 1.66. The most common processes are those involving the presence of hydrogen fluoride ("HF Processes") and those involving the use of a solid acidic catalyst ("Solid Catalyst Processes"). In general, the HF Process and the Solid Catalyst Process involve contacting an olefin with a stoichiometric excess of benzene at elevated temperature to produce alkylbenzene.

The amount of benzene present during the alkylation will depend upon the sought conversion selectivity to alkylbenzene. In general, the greater the stoichiometric excess of benzene, the greater the selectivity to alkylbenzene. Typically, the ratio of benzene to olefin during alkylation is within the range of about 5:1 to 50:1 or more. For the HF Processes, this ratio is often between about 5:1 to 10:1, and for the Solid Catalyst Processes, between about 10:1 to 30:1. The olefin-containing feed to the alkylation reactor should be sufficiently free of impurities, such as water and sulfur compounds that can unduly adversely affect the life of the alkylation catalyst.

U.S. Pat. No. 4,463,205, herein incorporated by reference in its entirety, discloses typical HF Processes. In these HF Processes, the reactants are normally subjected to vigorous mixing and agitation at the point of initial contact of the olefin and the liquid-phase hydrogen fluoride. The alkylation zone preferably has an overall arrangement similar to that shown in U.S. Pat. No. 3,494,971. In this arrangement, the two feed hydrocarbons and liquid phase HF are charged to a reactor. The effluent of this reactor is passed into a first settling zone and separated into HF and hydrocarbon phases. The HF is withdrawn and divided into a portion passed into a regenerator and a portion returned to the reactor. A hydrocarbon phase is withdrawn from the first settling zone and charged to a contactor, which is sometimes referred to as a second "reactor" as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as the alkylation zone effluent stream but is preferably passed into a stripping column in which dissolved HF is removed overhead and some of the feed aromatic hydrocarbon is also recovered. The net bottoms of this HF stripping column becomes the alkylation zone effluent stream charged to the fractionation zone of the subject process.

The alkylation reaction zone is maintained at alkylation conditions. As used herein in reference to HF processes, the term "alkylation conditions" is intended to include a pressure sufficient to maintain the reactants and HF in a liquid phase. A general range of operating pressures is from about 200 kPa(a) (29.0 psi(a)) to 4500 kpa(a) (653 psi(a)). The temperature range covered by this set of conditions is from about $-20°$ C. ($-4°$ F.) to about $95°$ C. ($203°$ F.), but the reaction is preferably conducted at a temperature of from $15°$ C. ($59°$ F.) to $70°$ C. ($158°$ F.). The volumetric ratio of HF to the total amount of hydrocarbons entering the reactor should be maintained within the broad range of from about 0.2:1 to about 10:1, preferably from 0.5:1 to 2:1.

The effluent streams leaving the reactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones. The two settling zones will normally be maintained at a temperature that is set by the entering HF-hydrocarbon mixtures withdrawn from the respective upstream zones. They will therefore be at substantially the same temperature as the immediately upstream reactor or contactor. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Regeneration of the HF catalyst is normally accomplished by stripping the acid under conditions sufficient to decompose alkylfluorides and to produce an overhead vapor stream containing HF and the stripping media. Benzene available within the process is a suitable stripping media. The overhead vapor stream of the column is passed into a condenser, the resultant condensate is allowed to separate into an acid phase and a benzene phase containing dissolved HF.

The overhead vapor stream of the HF regeneration column will contain vapor-phase HF and the benzene. This vapor stream has a low concentration of the higher boiling impurities. The higher boiling materials are concentrated into a relatively small stream removed from the HF regeneration column as a net bottoms stream. The benzene present in the overhead vapor stream of the HF regeneration column is derived mainly from the reflux liquid fed to the top of this column. A small amount of benzene is also dissolved in the liquid phase HF stream fed to HF regeneration column. The reflux liquid is preferably removed from the overhead receiver, which collects the condensed overhead of the HF stripping column. It is not necessary to supply reflux liquid for successful operation of the HF regeneration column if the feed stream is passed into the top of the column.

The hydrocarbonaceous phase removed from the second settling zone is preferably passed into a stripping column referred to as the HF stripping column. The function of this column is to prevent the passage of HF into the downstream fractionation zone. Representative conditions for the operation of the HF stripping column include an overhead vapor temperature of about 100° C. (212° F.) to 125° C. (257° F.) at a pressure of about 200 kPa(g) (29.0 psi(g)) to 300 kPa(g) (43.5 psi(g)). There is normally no external reflux to this column. The overhead vapor stream of the HF stripping column is normally condensed by cooling it to about 35° C. (95° F.) or less.

In the Solid Catalyst Processes, benzene and the olefin are reacted under alkylation conditions in the presence of a solid alkylation catalyst. These alkylation conditions generally include a temperature in the range between about 80° C. (176° F.) and about 200° C. (392° F.), most usually at a temperature not exceeding about 175° C. (347° F.). Since the alkylation is typically conducted in at least partial liquid phase, and preferably in either an all-liquid phase or at supercritical conditions, pressures must be sufficient to maintain reactants in the desired phase. The requisite pressure necessarily depends upon the olefin and temperature, but normally is in the range of about 1300 kpa(g) (189 psi(g)) to 7000 kpa(g) (1015 psi(g)), and most usually between about 2000 kpa(g) (290 psi(g)) and 3500 kpa(g) (508 psi(g)). Preferably the alkylation conditions do not result in substantial skeletal isomerization of the olefin. For instance, less than 15 mole percent, and preferably less than 10 mole percent, of the olefin, the aliphatic alkyl chain, and any reaction intermediate undergoes skeletal isomerization.

Alkylation of benzene by the olefins is conducted in a continuous manner, and one or more catalyst beds in flow series are used. For purposes herein, a catalyst bed is termed a reactor whether in the same or a separate vessel from another bed. In preferred processes of this invention 2 or 3 reactors can be used to achieve an advantageous combination of performance and capital expense avoidance.

The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone, and at each zone the benzene to olefin molar ratio may be greater than 50:1. The total feed mixture, that is, aromatic compound plus olefin, is often passed through the packed bed at a liquid hourly space velocity (LHSV) between about 0.3 and about 6 hr$^{-1}$ depending upon, e.g., alkylation temperature and the activity of the catalyst. Lower values of LHSV within this range are preferred.

Any suitable alkylation catalyst may be used in the present invention, provided that the requirements for conversion, selectivity, and activity are met. U.S. Pat. No. 5,196,574 (Kocal) and U.S. Pat. No. 5,344,997 (Kocal) describe alkylation of aromatics using a fluorided silica-alumina catalyst. U.S. Pat. No. 5,302,732 (Steigleder, et al.) describes alkylation of aromatics using an ultra-low sodium silica-alumina catalyst. The teachings of U.S. Pat. Nos. 5,196,574, 5,302, 732, and 5,344,997 are incorporated herein by reference. Preferred alkylation catalysts comprise zeolites having a zeolite framework type selected from the group consisting of BEA, MOR, MTW, and NES. Such zeolites include mordenite, ZSM-4, ZSM-12, ZSM-20, offretite, gmelinite, beta, NU-87, and gottardiite. Further discussion of alkylation catalysts can be found in U.S. Pat. Nos. 6,315,964 and 6,617,481.

In common commercial configurations, the alkylation reactor effluent would be passed to a distillation assembly that separates as a relatively pure stream the benzene contained in the effluent. The bottoms stream from this distillation assembly would then be passed to a distillation assembly to separate as the overhead, paraffins and unreacted olefins, and the bottoms from this second distillation assembly would be fed to a heavies distillation assembly where the alkylbenzene product is contained in the overhead. If desired, a finishing column may be used to further purify the alkylbenzene, especially after a clay treatment to remove color formers. In this common commercial configuration of distillation train, the bottoms stream for the lights distillation is normally fed to the distillation assembly for separating the benzene.

Typically the benzene distillation is generally conducted with a bottoms temperature of less than about 300° C. (572° F.), preferably less than about 275° C. (527° F.), usually between about 230° C. (446° F.) and 270° C. (518° F.), and at a pressure at which the overhead is provided of between about 5 kpa(g) (0.7 psi(g)) and 300 kPa(g) (43.5 psi(g)), preferably between about 35 kpa(g) (5.1 psi(g)) and 70 kpa(g) (10.2 psi(g)). The overhead generally contains less than about 2, preferably less than about 1.5, mass-percent paraffins. The benzene distillation assembly may comprise one or more distillation columns. More than one overhead may be obtained from the benzene distillation assembly. For instance, a highly pure stream may be obtained to provide a regenerant for regenerating the sorbent. A lesser purity overhead may be obtained from the benzene distillation assembly, e.g., as a side draw, for use as a recycle to the alkylation reaction.

Each column may contain any convenient packing or distillation trays, but most often trays such as sieve and bubble trays, are used. Often the assembly provides at least about 5, say 6 to 70, and preferably 20 to 50, theoretical plates. The reflux ratio (herein defined as the distillate to reflux mass ratio) is often in the range of about 2:1 to 1:10, preferably about 1.5:1 to 1:5. The bottoms stream from the benzene distillation generally contains less than about 1000 mppm, preferably less than about 50 mppm, and sometimes less than about 5 mppm, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C. (572° F.), preferably less than about 275° C. (527° F.), usually between about 250° C. (482° F.) and 275° C. (527° F.), and at a pressure at which overhead is provided of between about 5 kpa(a) (0.7 psi(a)) and 110 kPa(a) (16 psi(a)), preferably between about 10 kpa(a) (1.5 psi(a)) and 50 kPa(a) (7.3 psi (a)). The column may contain any convenient packing or distillation trays, but most often sieve trays are used. Often the paraffins distillation assembly provides at least about 5, say 7 to 20, theoretical plates. The reflux ratio is often in the range of about 3:1 to 1:10, preferably about 1:1 to 1:3. The bottoms stream from the paraffins distillation generally contains less than about 5000, preferably less than about 500, parts by million by mass (mppm) paraffins and preferably less than about 10, often less than about 1, mppm benzene. The overhead from the paraffins column generally contains less than about 1, preferably less than about 0.5, and most preferably less than about 0.2, mass-percent alkylbenzene. The paraffins distillation may occur in a single column or two or more distinct columns may be used.

The heavy alkylate distillation is generally conducted with a bottoms temperature of less than about 300° C. (572° F.), preferably less than about 275° C. (527° F.), usually between about 250° C. (482° F.) and 275° C. (527° F.), and at a pressure of between about 0.5 kpa(a) (0.07 psi(a)) and 30 kpa(a) (4.4 psi(a)), preferably between about 1 kPa(a) (0.14 psi(a)) and 5 kpa(a) (0.7 psi(a)). The column may contain any convenient packing or distillation trays, but most often structured packing is used. Often the heavy alkylate distillation assembly provides at least about 5, say 10 to 30, and preferably 10 to 20, theoretical plates. The reflux ratio is often in the range of about 2:1 to 1:5, preferably about 0.2:1 to 1:1. The overhead from the heavy alkylate distillation generally contains less than about 1000, preferably less than about 100 mppm, and sometimes less than about 50 mppm, total heavies.

The refining system may contain additional distillation zones, e.g., to recover additional alkylbenzene from heavies. At least a portion of the heavies-containing stream may be recycled to the dealkylation process for recovery of benzene.

The invention will be further illustrated with reference to the drawings, which are not intended to be in limitation of the breadth of the invention.

With reference to FIG. 1, an aliphatic, mono-olefin-containing feedstock is supplied via line 102 to sorber assembly 104. In sorber assembly 104, aromatic by-products in the feedstock are selectively sorbed to provide a sorption effluent having a reduced content of aromatic by-products. The sorption effluent is withdrawn from sorber assembly 104 via line 106 and passed to alkylation reactor assembly 108 where mono-olefin is reacted with benzene to produce alkylbenzene. A reaction effluent is passed from reactor assembly 108 via line 110 to benzene column 112. Benzene column 112 provides a bottoms stream containing alkylbenzene which is withdrawn via line 114 for further refining. If the feedstock contains paraffins, the paraffins would also be present in the bottoms stream. As shown two overhead streams are taken from benzene column 112. One stream is passed via line 116 to be recycled to reactor assembly 108. The other stream is passed via line 118 for use as the regenerant for sorber assembly 104.

Sorber assembly 104 contains a plurality of sorber beds 120, each of which is able to be on-stream (sorbing aromatic by-products from the feedstream) or off-stream. An off-stream bed may undergo a purging and regeneration operation and then be cycled to an on-stream condition. The overhead stream in line 118 from benzene column 112 is highly pure benzene and is used as the regenerant for the regeneration of a sorber bed 120 that is off-stream. The benzene is passed through the bed and displaces or desorbs aromatic by-product. A spent regenerant stream is produced, i.e., a regeneration effluent, which contains in addition to benzene, the removed aromatic by-products. The regeneration effluent is passed via line 122 to the regeneration effluent distillation system. As depicted, the regeneration effluent distillation system comprises distillation column 124 which receives as a feed regeneration effluent via line 122. Column 124 provides a benzene-containing overhead and a bottoms fraction containing higher boiling components including the removed aromatic by-products.

These higher boiling components are passed from column 124 to dealkylation reactor 130 via line 126. Hydrogen for the dealkylation is provided to line 126 via line 128. In dealkylation reactor 130, at least a portion of the aromatic by-products are converted to benzene. A benzene product stream is withdrawn from reactor 130 via line 132 and passed to phase separator 134 where gaseous hydrogen in the overhead is recycled to reactor 130 via line 136. The liquid phase containing benzene is passed via line 138 to column 124 as another feed. While a separate column could be used to separate the liquid phase, the separation of the liquid phase to be effected is similar to that of the regeneration effluent in column 124 and thus if capacity exists, the same distillation column is used for both separations. The unreacted aromatic by-products in the benzene product stream are returned to the bottoms fraction and are thus recycled to dealkylation reactor 130. A purge is taken via line 140 to prevent undue buildup in the cycle loop defined by the regeneration effluent distillation system and the dealkylation reactor.

The benzene product stream in line 138 also contains components that have lower boiling points than does benzene. These lights comprise coproducts and by-products of the dealkylation. The overhead in column 124 contains benzene and these lights and is passed via line 142 to lights column 144. Lights column 144 provides a bottoms stream rich in benzene which stream is withdrawn via line 146 and passed to reactor assembly 108 to supplement the benzene for the benzene alkylation reaction. The overhead in lights column 144 is primarily paraffins having from 1 to 5 carbon atoms per molecule and is passed via line 148 to sorber assembly 104 to purge a sorber bed 120 prior to regeneration. The lights purge will remove non-sorbed components from the bed including benzene, olefins and, if present in the feedstock, paraffins. The purge containing these components is passed from sorber assembly 104 to lights column 144 via lines 150 and 142. The heavier olefins and paraffins go to the bottoms fraction during the distillation and are thus passed from lights column 144 to reactor assembly 108 via line 146. A purge is taken from line 148 via line 152 to prevent undue buildup of lights in the cycle loop defined by lights column 144 and sorber assembly 104. The purge in line 152 may be used for any suitable purpose including for burning to recover its heat value.

Undue buildup of lights in the cycle loop can result in incomplete condensation of the overhead stream of lights column 144. Undue buildup of lights can also lead to excessive light material in the benzene-containing bottom stream of the lights column. The benzene product stream can be considered to be relatively free of light material when it contains less than 5 mass-%, or more preferably less than 2 mass-% or most preferably less than 1 mass-% of light material that boils below the boiling point of the purge component. It is expected that the purge stream in line 254 will be set to at least 1 mass-%, possibly at least 2 mass-%, and in some cases at least 5 mass-% of the lights column overhead stream.

Figure 2:
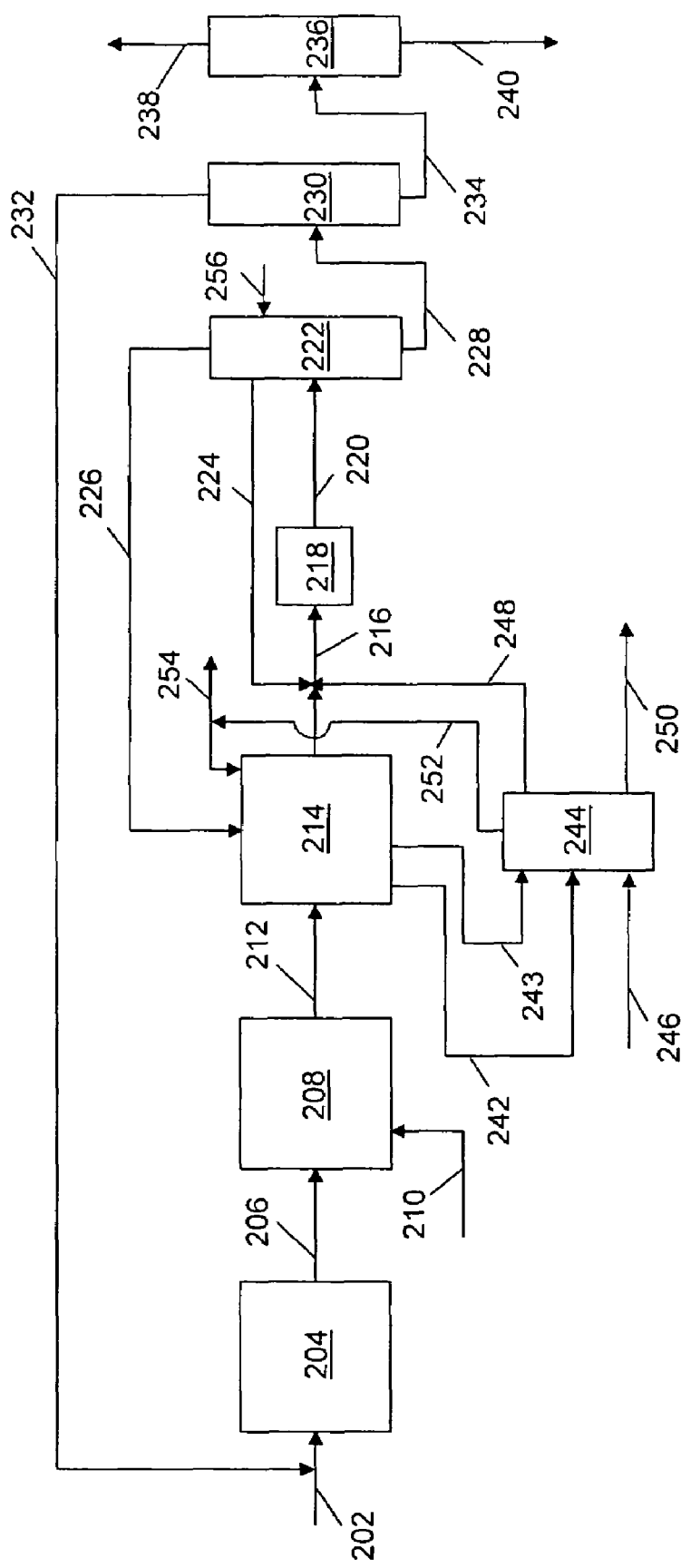
FIG. 2 is a schematic depiction of a process flow scheme in accordance with this invention for an integrated process for dehydrogenating a paraffin to produce an olefin-containing feedstock and using the olefin-containing feedstock for the alkylation of benzene.

FIG. 2 is a schematic depiction of an integrated paraffin dehydrogenation and benzene alkylation process. Paraffin is supplied via line 202 to dehydrogenation section 204 to provide an olefin-containing feedstock. The olefin-containing feedstock is passed via line 206 to selective hydrogenation section 208 to convert diolefins to mono-olefins. Hydrogen is supplied to selective hydrogenation section via line 210. The olefin-containing feedstock is then passed from selective hydrogenation section 208 via line 212 to sorber assembly 214 to remove aromatic by-products by sorption and provide a sorption effluent stream which is passed via line 216 to alkylation reactor assembly 218.

The alkylation reaction effluent from alkylation reactor 218 is passed via line 220 to the alkylbenzene refining section. As shown, the alkylation reaction effluent is first passed to benzene column 222 which provides a benzene-containing overhead stream which is recycled via line 224 to alkylation reactor assembly 218 and another benzene-containing overhead stream that is recycled via line 226 as regenerant to sorber assembly 214. The bottoms of benzene column 222 contain paraffins and alkylbenzenes as well as heavies such as dialkylbenzenes produced during the alkylation. The bottoms are passed to paraffins column 230 via line 228. Paraffins column 230 provides a paraffin-rich overhead that is recycled via line 232 as part of the paraffin feed to dehydrogenation section 204. The bottoms of paraffins column 230 contain alkylbenzenes and heavies and are passed via line 234 to product column 236. The refined alkylbenzene product is obtained via line 238 as an overhead stream, and a heavies-containing bottoms is withdrawn from product column 236 via line 240.

Sorber assembly 214 contains beds of sorbent that cycle between on-line and off-line. When off-line, a bed is purged and regenerated using benzene supplied via line 226. The regeneration effluent containing the benzene and aromatic by-products removed from the bed being regenerated is passed via line 242 to regeneration effluent distillation and dealkylation reactor assembly 244. This assembly may be of any suitable design, including, but not limited to, those depicted in FIGS. 1 and 3. Hydrogen is supplied to the assembly via line 246. A benzene stream from assembly 244 is passed via lines 248 and 216 to alkylation reactor assembly 218, and a purge containing heavies such as unreacted aromatic by-products, is removed from the assembly 244 via line 250. Assembly 244 also provides a lights stream containing paraffins having from 1 to 5 carbon atoms per molecule. This lights stream is directed to sorber assembly 214 via line 252 to purge a bed of sorbent prior to regeneration. The purge is recycled to assembly 244 via line 243. Alternatively, some or all of this purge can be recycled to assembly 244 via line 242. Line 254 removes a portion of the lights stream to prevent undue buildup of lights in the cycle loop defined by assembly 244 and sorber assembly 214.

The benzene that passes to the alkylation reactor assembly 218 is supplied by the benzene-containing overhead stream recycled via line 224 and by the benzene stream in line 248. In one embodiment aromatic by-products may be substantially absent from the benzene stream in line 248. If the benzene stream in line 248 contains aromatic by-products, then the mole ratio of benzene to aromatic by-products passed to the alkylation reactor assembly 218 is preferably greater than 95:5 and more preferably greater than 98:2. This helps ensure that olefins are efficiently reacted in the alkylation reactor assembly 218 to form the desired product.

In the practice of the process schematically depicted in FIG. 2, a number of benefits can be realized due to the integration in accordance with this aspect of the present invention. First, a portion of the benzene for the alkylation is obtained from aromatic by-products that would otherwise have value only as fuel. Second, the dehydrogenation of paraffin may be conducted under more severe conditions yet still provide an economically attractive process when integrated with a benzene alkylation process. The increased aromatic by-products that result from using the more severe conditions can be used to recover useful benzene.

A higher olefin to paraffin ratio in the dehydrogenation effluent reduces the capital and operating costs of the alkylation process per unit of production since with less paraffin per mole of olefin, the total mass of fluid to be handled such as by pumping and transporting, changing temperature, and vaporizing in distillations decreases. For example, an increase in the mole ratio of olefin:paraffin from 1:10 to 1:5 can reduce the mass load on the benzene distillation column by nearly 20 percent resulting in either substantial capital and operating savings or in the ability to increase capacity. As about 50 percent of the reboiler heat required for refining the alkylbenzene reaction effluent is consumed in the benzene column reboiler, this savings can be material to plant economics. Similarly, the load on the paraffin distillation column will be reduced by nearly 50 percent. As the paraffin column is usually operated at a substantial vacuum in order to avoid reboiler temperatures that can result in undue degradation of alkylbenzenes, reboiler and vacuum cost savings are both realized.

A third advantage is that the amount of benzene required to be externally supplied is reduced. The dehydrogenation section can often be operated to generate, in combination with the processes of this invention, at least about 10, and sometimes from about 20 to 70, percent of the benzene requirements. The sum of the moles of benzene generated by or derived from the dehydrogenation section and the moles of benzene generated by or derived from the dealkylation reactor assembly to the moles of olefins generated by or derived from the dehydrogenation section is in a ratio of at least about 0.1:1, and sometimes from about 0.2:1 to 0.7:1. This generated benzene is relatively free from impurities such as water and nitrogen compounds that can be adverse to the alkylation catalyst.

Fourth, especially where capacity increases in existing processes are sought, sorber assemblies often have the ability to handle increased flows of olefin-containing feedstock including feedstocks containing increased amounts of aromatic by-products though increasing cycle times.

A fifth advantage is that the processes of the invention can often be readily retrofitted into existing integrated plants that dehydrogenate paraffins to provide feedstocks for making alkylbenzenes. Generally these plants already use a sorber assembly to remove aromatic by-products and a regeneration effluent distillation system. This equipment is often adequately sized for use in the processes of this invention, and the equipment needed to be added will exclusively relate to the dealkylation reactor and the cycle loop to and from the distillation system.

A sixth advantage is that if the paraffins column is pushed beyond capacity or is operated such that alkylbenzene is contained in the overhead, the processes of this invention enable recovery of the benzene values.

Figure 3:
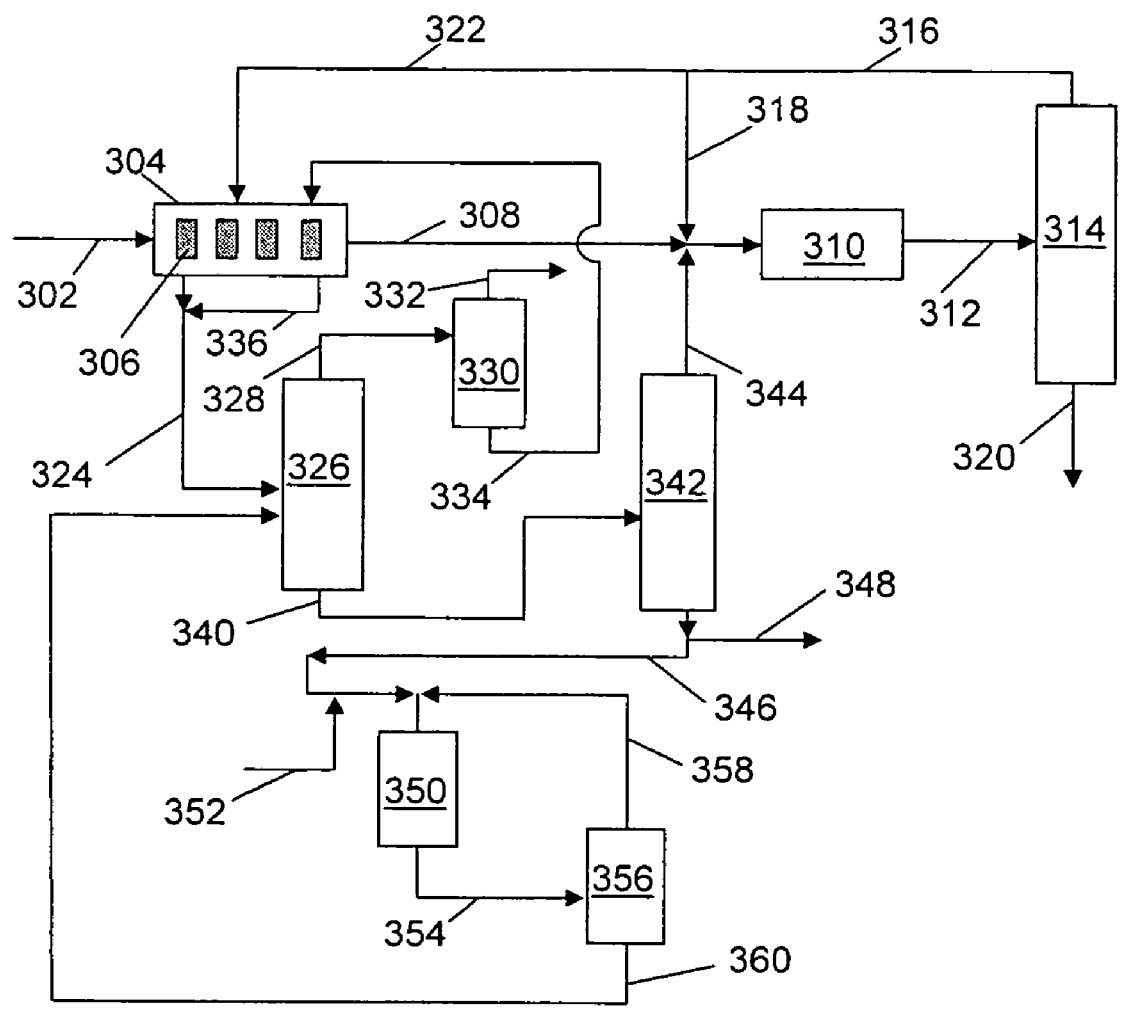
FIG. 3 is a schematic depiction of another process flow scheme in accordance with this invention for treating an olefin-containing feedstock.

FIG. 3 depicts another regeneration effluent distillation system configuration useful in the practice of this invention. Mono-olefin-containing feedstock is supplied via line 302 to sorber assembly 304. Sorber assembly 304 contains a plurality of sorber beds 306, each of which can cycle between on-stream and off-stream operation. In sorber assembly 304, aromatic by-products are removed from the feedstock to provide a sorption effluent which is passed via line 308 to alkylation reactor assembly 310 for reaction with benzene to produce alkylbenzene. The alkylation reaction effluent passes from reactor assembly 310 to benzene distillation column 314 via line 312. The overhead from column 314 is rich in benzene and is withdrawn via line 316. A portion of the overhead in line 316 is passed for recycle to alkylation reactor assembly 310 via line 318. The bottoms in benzene distillation column 314 are withdrawn via line 320 for further refining.

Another portion of the overhead in line 316 is withdrawn via line 322 for use as regenerant in sorber assembly 304. The regenerant desorbs or displaces aromatic by-products from the sorbent and the regeneration effluent is passed via line 324 to lights column 326. Lights column 326 takes as an overhead components boiling below benzene such as paraffins having from 1 to 5 carbon atoms per molecule. The overhead from lights column 326 is passed via line 328 to purging fluid column 330. In purging fluid column 330, desired higher molecular weight lights for purging a sorber bed prior to regeneration are separated as a bottoms stream and lighter components are discharged as overhead via line 332. These lighter components can be used for any suitable purpose including for fuel value. The bottoms pass through line 334 to sorber assembly 304 for purging a bed prior to regeneration. A purge effluent is produced containing components that had been in the interstices of the bed and is passed via line 336 to lights column 326.

The bottoms from lights column 326 contains benzene, the components that had been in the interstices of the bed, and aromatic by-products. The bottoms are directed via line 340 to aromatics column 342 which provides an overhead, benzene-rich stream that is passed via line 344 to alkylation reactor assembly 310 and an aromatic by-products-rich bottoms. A portion of the bottoms is directed by line 346 to dealkylation reactor 350. Another portion of the bottoms is purged via line 348. Hydrogen for the dealkylation is provided to dealkylation reactor 350 via line 352. In dealkylation reactor 350, benzene is formed from aromatic by-products to provide a benzene product stream. This stream is passed via line 354 to phase separator 356. A hydrogen-rich gaseous phase is recycled to dealkylation reactor 350 via line 358. A portion of the gaseous phase may be purged and used for fuel value. The benzene-containing liquid phase is recycled to lights column 326 via line 360.

Components that had been in the interstices of the bed and that are directed by line 346 to dealkylation reactor 350 may crack at dealkylation conditions. To minimize cracking if these components are valued, a variation of the flow scheme of FIG. 3 could be used in which the purge effluent in line 336 is passed to a purge effluent distillation column rather than lights column 326. The purge effluent column would take as an overhead desired lights for purging and lighter components. The overhead from the purge effluent column would pass to purging fluid column 330. The purge effluent column bottoms would contain components that had been in the interstices of the bed and would be passed to alkylation reactor 310.

Figure 4:
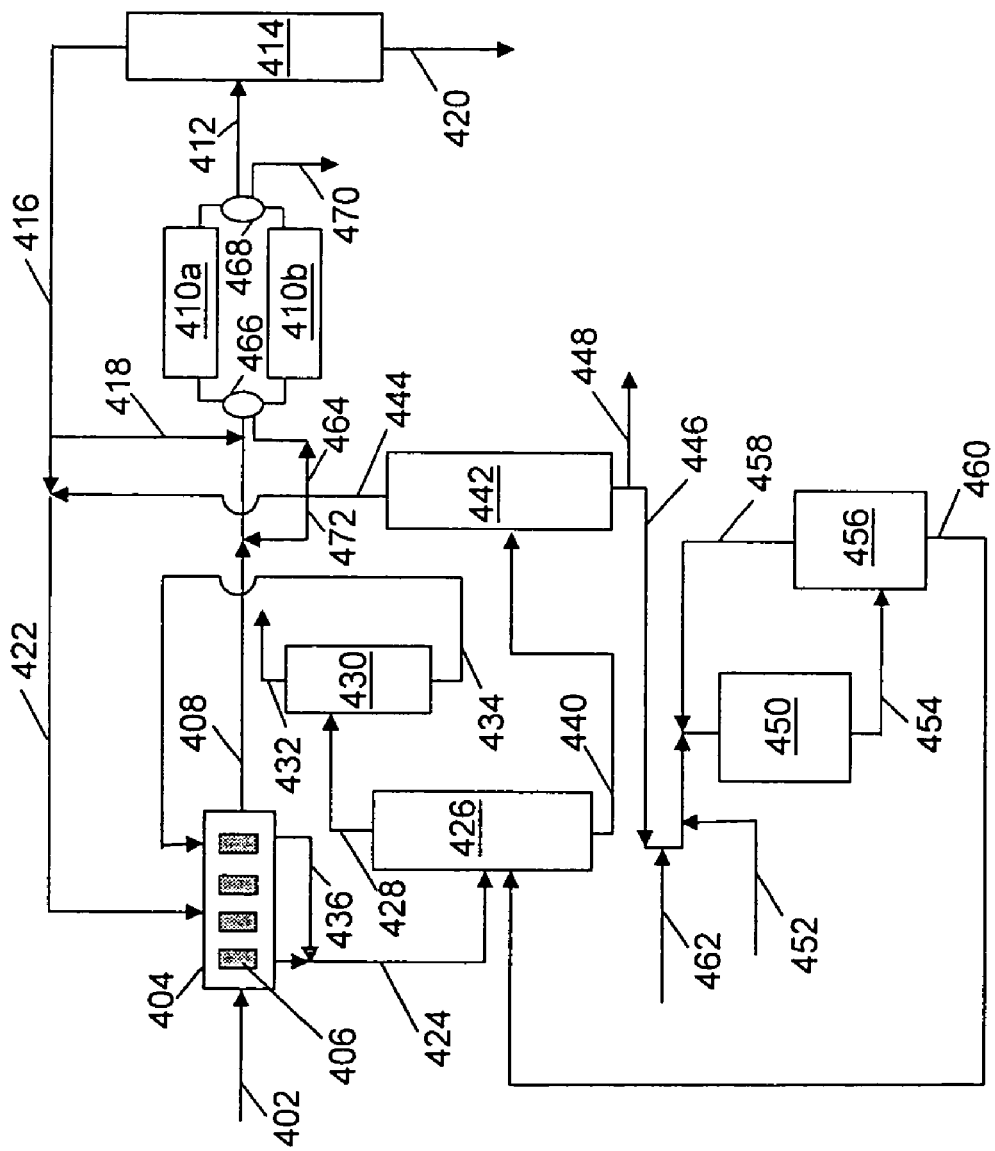
FIG. 4 is schematic depiction of a further process flow scheme in accordance with this invention for treating an olefin-containing feedstock in which benzene from the dealkylation is used for regenerating alkylation catalyst.

FIG. 4 depicts another regeneration effluent distillation system configuration useful in the practice of this invention. Mono-olefin-containing feedstock is supplied via line 402 to sorber assembly 404. Sorber assembly 404 contains a plurality of sorber beds 406, each of which can cycle between on-stream and off-stream operation. In sorber assembly 404, aromatic by-products are removed from the feedstock to provide a sorption effluent which is passed via line 408 to alkylation reactor assembly 410 for reaction with benzene to produce alkylbenzene. The alkylation reaction effluent passes from reactor assembly 410 (shown as having two reactors 410a and 410b) to benzene distillation column 414 via line 412. The overhead from column 414 is rich in benzene and is withdrawn via line 416. All or a portion of the overhead in line 416 is passed for recycle to alkylation reactor assembly 410 via line 418. Any remaining portion can be used to supplement the benzene-containing stream in line 444 for regenerating sorber beds via line 422. The bottoms in benzene distillation column 414 are withdrawn via line 420 for further refining.

A benzene-containing stream provided by line 422 is used as regenerant in sorber assembly 404. The regenerant desorbs or displaces aromatic by-products from the sorbent and the regeneration effluent is passed via line 424 to lights column 426. Lights column 426 takes as an overhead components boiling below benzene such as paraffins having from 1 to 5 carbon atoms per molecule. The overhead from lights column 426 is passed via line 428 to purging fluid column 430. In purging fluid column 430, desired higher molecular weight lights for purging a sorber bed prior to regeneration are separated as a bottoms stream and lighter components are discharged as overhead via line 432. These lighter components can be used for any suitable purpose including for fuel value. The bottoms pass through line 434 to sorber assembly 404 for purging a bed prior to regeneration. A purge effluent is produced containing components that had been in the interstices of the bed and is passed via line 436 to lights column 426.

The bottoms from lights column 426 contains benzene, the components that had been in the interstices of the bed and aromatic byproducts. The bottoms are directed via line 440 to aromatics column 442 which provides an overhead, benzene-rich stream that is withdrawn via line 444. Advantageously, this benzene-rich stream can be used in several ways. A portion of the benzene-rich stream is passed via line 422 for use as the regenerant. Another portion of the benzene-rich stream is passed via line 472 to alkylation reactor assembly 410. A third portion of the benzene-rich overhead is used to regenerate catalyst in alkylation reactor assembly 410.

Components that had been in the interstices of the bed and that are directed by line 446 to dealkylation reactor 450 may crack at dealkylation conditions. If these components are valued, a variation of the flow scheme of FIG. 4 could be used to minimize cracking. The purge effluent in line 436 could be passed to a purge effluent distillation column rather than lights column 426. The purge effluent column would take as an overhead desired lights for purging and lighter components. The overhead from the purge effluent column would pass to purging fluid column 430. The purge effluent column bottoms would contain components that had been in the interstices of the bed and would be passed to alkylation reactor 410.

Column 442 also provides an aromatic by-products-rich bottoms. A portion of the bottoms is directed by line 446 to dealkylation reactor 450. Another portion of the bottoms is purged via line 448. Hydrogen for the dealkylation is provided to dealkylation reactor 450 via line 452. Make-up benzene for the alkylation is provided via line 462 and is also passed to dealkylation reactor 450.

In dealkylation reactor 450, benzene is formed from aromatic by-products to provide a benzene product stream. The dealkylation may be a thermal dealkylation or a catalytic dealkylation. Where the make-up benzene contains undesirable impurities such as oxygenates and nitrogen or sulfur-containing compounds, the dealkylation conditions are often sufficient to crack these components to lights that can be removed from the process through line 432. Acidic dealkylation catalysts may be preferred since they are more active in cracking heterocyclic compounds that may contaminate the benzene such as dioxane. The benzene product stream from dealkylation reactor 450 is passed via line 454 to phase separator 456. A hydrogen-rich gaseous phase is recycled to dealkylation reactor 450 via line 458.

A benzene-containing liquid phase from phase separator 456 is recycled to lights column 426 via line 460. This stream also contains added benzene for make-up for the alkylation and by-products from the purification of the make-up benzene. Lights column 426 separates the benzene and heavier components from the lighter components, including these by-products.

In the system depicted in FIG. 4, aromatics column 442 is operated to provide a benzene overhead substantially free of olefin and paraffin in the feedstock, e.g., detergent range aliphatic compounds of greater than about 8 carbon atoms per molecule. Thus the benzene-containing overhead would be suitable for the regeneration of the alkylation catalyst. A portion of the overhead from aromatics column 442 is passed via line 464 to valve assembly 466. Valve assembly 466 directs the sorption effluent from line 408 to either alkylation reactor assembly 410*a* or 410*b* with the other reactor assembly undergoing regeneration using benzene from line 464 directed thereto by valve assembly 466.

The effluents from alkylation reactor assemblies 410*a* and 410*b* are directed to valve assembly 468. The alkylation reactor effluent from the reactor assembly on-line is directed by line 412 to benzene column 414. The spent benzene from the catalyst regeneration is directed by valve assembly to line 470. The spent benzene may be used as fuel value or may be passed to dealkylation reactor 450 wherein arylalkanes would be dealkylated and aliphatic compounds cracked to lights. Alternatively, the spent benzene may be passed either to column 442, where benzene is recovered directly, and any heavies are routed to the dealkylation reactor 450 or to column 414 along with the reactor product, for further purification.

By way of example and not in limitation of the invention, an integrated paraffin dehydrogenation and benzene alkylation facility such as described in FIG. 2 to alkylate benzene is modeled. The five runs of the model described herein are prophetic and are based on actual pilot plant and commercial operations, on engineering calculations, and on experience with similar processes. The facility is modeled with a first olefin feedstock rich in aliphatics having 10 to 13 carbon atoms per molecule (Feedstock A). A paraffinic feedstock is converted to Feedstock A by dehydrogenation followed by selective hydrogenation. The composition of Feedstock A is set forth in Table 1.

TABLE 1

Feedstock A

| Component | Mass-percent |
| --- | --- |
| $C_{10}$ paraffins | 8.36 |
| $C_{10}$ olefins | 0.95 |
| $C_{11}$ paraffins | 35.05 |
| $C_{11}$ olefins | 4.45 |
| $C_{12}$ paraffins | 25.62 |
| $C_{12}$ olefins | 3.64 |
| $C_{13}$ paraffins | 17.46 |
| $C_{13}$ olefins | 2.78 |
| Aromatics | 0.71 |
| Other | balance |

Run I (Comparative)

Essentially all of the aromatics in Feedstock A are removed in sorber assembly 214. The regenerant for sorber assembly 214 is a benzene-rich stream from benzene column 222. A regeneration effluent distillation system such as depicted in FIG. 1 is used, but without using the dealkylation reactor, i.e., the cycle loop containing the dealkylation reactor is not used. The benzene separated from the regeneration effluent is returned to the alkylation reactor assembly.

Alkylation reactor assembly 218 uses a solid acid catalyst such as described as Catalyst G in U.S. Pat. No. 5,196,574 to provide an alkylation reaction effluent. After removal of benzene in benzene column 222 the composition fed to paraffin column 230 is expected to be as set forth in Table 2.

TABLE 2

Paraffin Column Feed Using Feedstock A in Run I

| Component | Mass-percent |
| --- | --- |
| Alkylbenzenes | 15.99 |
| Paraffins | 82.95 |
| Other | balance |

The alkylation product is refined as described in connection with FIG. 2 to provide an alkylbenzene product containing about 99.3 mass-percent alkylbenzene.

Run II

Run I is essentially repeated except that the cycle loop is used to treat the aromatic by-products. The feed to the dealkylation reactor contains 83.3 mass-percent aromatics and 17.7 mass-percent total aliphatics. About 6.8 kg of hydrogen are provided per 100 kg of feed to the dealkylation reactor. The regeneration effluent distillation and dealkylation reactor assembly 244 uses a thermal hydrodealkylation reactor that is operated at a temperature of about 620° C. (1202° F.) and a pressure of 3200 kPa(g) (464 psi(g)). The benzene provided by the dealkylation is about 3.7 mass-percent of the make-up benzene required. The compositions of the feed to paraffin column 230 and the alkylbenzene product for Run II are substantially the same as those for Run I. For this run, the modeling assumes a constant rate of alkylbenzene production.

Run III (Comparative)

Run II is essentially repeated except that the dehydrogenation of the paraffinic feedstock is conducted under more severe conditions. The composition of the olefin feedstock (Feedstock B) after dehydrogenation and selective hydrogenation (assuming the same selective hydrogenation conditions as in Run II) is set forth in Table 3.

TABLE 3

Feedstock B

| Component | Mass-percent |
| --- | --- |
| $C_{10}$ paraffins | 7.92 |
| $C_{10}$ olefins | 1.37 |
| $C_{11}$ paraffins | 32.54 |
| $C_{11}$ olefins | 6.33 |
| $C_{12}$ paraffins | 23.51 |
| $C_{12}$ olefins | 5.16 |
| $C_{13}$ paraffins | 15.81 |
| $C_{13}$ olefins | 3.93 |
| Aromatics | 2.15 |
| Other | balance |

The selectivity of the conversion of the paraffin feedstock to Feedstock B is somewhat less than that for Feedstock A in that about 9 mass-percent more paraffin feedstock is used.

Due to the higher olefin to paraffin ratio of Feedstock B, for a given alkylbenzene production rate, the feed rate of Feedstock B is about 70 mass-percent of that required for Feedstock A.

Feedstock B is treated in sorber assembly 214 and the sorption effluent stream is fed to alkylation reactor assembly 218. No dealkylation operation is performed. After removal of benzene in benzene column 222 the composition fed to paraffin column 230 is expected to be as set forth in Table 4.

TABLE 4

Paraffin Column Feed Using Feedstock B in Run III

| Component | Mass-percent |
|---|---|
| Alkylbenzene | 22.43 |
| Paraffins | 75.66 |
| Other | balance |

Since a lesser concentration of paraffin is contained in Feedstock B than in Feedstock A, the heat duties for the benzene and paraffin columns are reduced. The alkylation product stream contains about 99 mass-percent alkylbenzene at the same production rate as in Run I.

Run IV

Run III is essentially repeated except that the cycle loop is used to treat the aromatic by-products. The feed to the dealkylation reactor contains 83.3 mass-percent aromatics and 17.7 mass-percent total aliphatics. About 6.8 kg of hydrogen are provided per 100 kg of feed to the dealkylation reactor. The regeneration distillation and dealkylation reactor assembly 244 uses a thermal hydrodealkylation reactor that is operated at about 620° C. (1202° F.) and a pressure of 3200 kPa (g) (464 psi(g)). The benzene provided by the dealkylation is about 10.5 mass-percent of the make-up benzene required. The compositions of the feed to paraffin column 230 and the alkylbenzene product for Run IV are substantially the same as those for Run III. For this run, the modeling assumes a constant rate of alkylbenzene production.

Run V

Run IV is essentially repeated except that the heavies stream in line 240 from product column 236 is directed to the dealkylation reactor in the regeneration effluent distillation and dealkylation reactor assembly 244. At constant alkylbenzene production rate and purity, the benzene from the dealkylation reactor provides about 15.4 mass-percent of the fresh benzene requirements for the process. The hydrogen to the dealkylation reactor is increased to about 9.4 mass-percent based on the combined feeds from the sorber assembly and the product column.

It is claimed:

1. An integrated process for producing an alkylbenzene, the process comprising:
    a) dehydrogenating a feedstock comprising a paraffin having from 6 to 22 carbon atoms per molecule in a dehydrogenation zone and recovering therefrom a dehydrogenated product comprising a mono-olefin, less than 85 mass-percent paraffins, benzene and at least about 2 mass-percent aromatic by-products having from 7 to 22 carbon atoms per molecule;
    b) selectively removing at least a portion of the aromatic by-products from at least a portion of the dehydrogenated product by at least intermittently passing at least a portion of the dehydrogenated product to an on-stream zone containing sorbent at conditions effective to selectively sorb aromatic by-products on the sorbent and to produce a sorption effluent stream comprising the mono-olefin and the paraffin and having a reduced concentration of aromatic by-products;
    c) regenerating the sorbent in an off-stream zone containing sorbent, the sorbent in the off-stream zone having aromatic by-products sorbed thereon from having been on-stream in step b, said regeneration comprising at least intermittently passing a regenerant containing benzene to the off-stream zone to desorb aromatic by-products from the sorbent and produce a regeneration effluent comprising benzene and aromatic by-products;
    d) distilling in a regeneration effluent distillation system at least a portion of the regeneration effluent to provide at least one overhead containing benzene and at least one higher-boiling fraction containing desorbed aromatic by-products;
    e) subjecting at least intermittently at least a portion of the at least one higher-boiling fraction to benzene-forming conditions to convert aromatic by-products to benzene and provide a conversion effluent containing benzene;
    f) distilling in the regeneration effluent distillation system at least a portion of the conversion effluent;
    g) alkylating benzene with at least a portion of the sorption effluent stream under alkylation conditions including a stoichiometric excess of benzene to provide an alkylation effluent comprising the alkylbenzene, the paraffin and benzene; and
    h) passing at least intermittently at least a portion of the at least one overhead containing benzene from step d to step g.

2. The process of claim 1 wherein said passing of at least a portion of the at least one overhead to step g comprises distilling the at least a portion of the at least one overhead to provide a lights-containing overhead and a liquid phase side-draw containing benzene and passing at least a portion of the liquid phase side-draw containing benzene to step g.

3. The process of claim 1 wherein the mole ratio of benzene derived from step a and step e to olefin derived from step a is at least about 0.1:1.

4. The process of claim 1 wherein the dehydrogenated product contains less than about 70 mass-percent paraffins.

5. The process of claim 4 wherein said at least intermittently passing of at least a portion of the dehydrogenated product to the on-stream zone comprises at least intermittently subjecting at least a portion of the dehydrogenated product to selective hydrogenation conditions including the presence of selective hydrogenation catalyst and hydrogen, said selective hydrogenation conditions being capable of selectively hydrogenating diolefins to mono-olefins and of producing a hydrogenated effluent, and at least intermittently passing at least a portion of the hydrogenated effluent to the on-stream zone.

6. The process of claim 1 wherein at least a portion of the alkylation effluent is distilled to remove benzene and to provide a benzene-depleted effluent, at least a portion of the benzene removed from the at least a portion of the alkylation effluent is recycled to step g, at least a portion of the benzene-depleted effluent is distilled to remove paraffin, and at least a portion of the paraffin removed from the at least a portion of the benzene-depleted effluent is recycled to step a.

7. The process of claim 6 wherein at least a portion of the benzene removed from the at least a portion of the alkylation effluent is used as the regenerant in step b.

8. The process of claim 7 wherein said distillation of the at least a portion of the alkylation effluent provides a benzene-containing stream having a concentration of benzene of at least 99.5 percent by mass.

9. The process of claim 1 wherein steps d, e and f define a flow cycle loop and wherein a purge is at least intermittently withdrawn from at least one point in the flow cycle loop in an amount sufficient to avoid undue buildup of aromatic by-products in the flow cycle loop.

* * * * *